(12) United States Patent
Simon et al.

(10) Patent No.: US 7,621,963 B2
(45) Date of Patent: Nov. 24, 2009

(54) COMPOSITE BONE GRAFT MATERIAL

(75) Inventors: Bruce J. Simon, Mountain Lakes, NJ (US); Robert M. Ronk, Pierceton, IN (US); Paul D'Antonio, Morristown, NJ (US); Jeffrey D. Schwardt, Palo Alto, CA (US)

(73) Assignee: EBI, LLC, Parsippany, NJ (US)

( * ) Notice: Subject to any disclaimer, the term of this patent is extended or adjusted under 35 U.S.C. 154(b) by 344 days.

(21) Appl. No.: 11/402,312

(22) Filed: Apr. 11, 2006

(65) Prior Publication Data

US 2006/0233851 A1 Oct. 19, 2006

Related U.S. Application Data

(63) Continuation-in-part of application No. 11/105,334, filed on Apr. 13, 2005.

(51) Int. Cl.
*A61F 2/28* (2006.01)
(52) U.S. Cl. .............. 623/23.61; 623/23.56; 623/23.58; 623/16.11; 623/23.62; 623/23.63; 424/682; 424/422; 424/426
(58) Field of Classification Search .................. None
See application file for complete search history.

(56) References Cited

U.S. PATENT DOCUMENTS

| | | |
|---|---|---|
| 4,168,326 A | 9/1979 | Broemer et al. |
| 4,365,356 A | 12/1982 | Broemer et al. |
| 4,636,526 A | 1/1987 | Dorman et al. |
| 4,698,375 A | 10/1987 | Dorman et al. |
| 4,769,011 A | 9/1988 | Swaniger |
| 4,842,604 A | 6/1989 | Dorman et al. |
| 5,034,352 A | 7/1991 | Vit et al. |
| 5,061,286 A | 10/1991 | Lyle |
| 5,064,436 A | 11/1991 | Ogiso et al. |
| 5,181,918 A | 1/1993 | Brandhorst et al. |
| 5,236,456 A | 8/1993 | O'Leary et al. |
| 5,240,659 A | 8/1993 | Ichitsuka et al. |
| 5,262,166 A | 11/1993 | Liu et al. |
| 5,273,964 A | 12/1993 | Lemons |
| 5,279,555 A | 1/1994 | Lifshey |
| 5,281,265 A | 1/1994 | Liu |
| 5,284,655 A | 2/1994 | Bogdansky et al. |
| 5,290,558 A | 3/1994 | O'Leary et al. |
| 5,298,254 A | 3/1994 | Prewett et al. |
| 5,314,476 A | 5/1994 | Prewett et al. |
| 5,338,772 A | 8/1994 | Bauer et al. |
| 5,344,654 A | 9/1994 | Rueger et al. |
| 5,366,507 A | 11/1994 | Sottosanti |
| 5,478,355 A | 12/1995 | Muth et al. |
| 5,482,717 A | 1/1996 | Fues et al. |
| 5,484,601 A | 1/1996 | O'Leary et al. |
| 5,507,813 A | 4/1996 | Dowd et al. |
| 5,543,156 A | 8/1996 | Roorda et al. |
| 5,545,409 A | 8/1996 | Laurencin et al. |
| 5,552,454 A | 9/1996 | Kretschmann et al. |
| 5,591,232 A | 1/1997 | Rahimi et al. |
| 5,614,206 A | 3/1997 | Randolph et al. |
| 5,618,549 A | 4/1997 | Patat et al. |
| 5,676,720 A | 10/1997 | Ducheyne et al. |
| 5,707,962 A | 1/1998 | Chen et al. |
| 5,756,127 A | 5/1998 | Grisoni et al. |
| 5,776,193 A | 7/1998 | Kwan et al. |
| 5,807,567 A | 9/1998 | Randolph et al. |
| 5,824,084 A | 10/1998 | Muschler |
| 5,888,967 A | 3/1999 | Honold et al. |
| 5,922,025 A | 7/1999 | Hubbard |
| 5,997,624 A | 12/1999 | Chow et al. |
| 6,001,394 A | 12/1999 | Daculsi et al. |
| 6,030,635 A | 2/2000 | Gertzman et al. |
| 6,030,636 A | 2/2000 | Randolph et al. |
| 6,180,605 B1 | 1/2001 | Chen et al. |
| 6,180,606 B1 | 1/2001 | Chen et al. |
| 6,187,046 B1 | 2/2001 | Yamamoto et al. |
| 6,187,047 B1 | 2/2001 | Kwan et al. |
| 6,189,537 B1 | 2/2001 | Wolfinbarger, Jr. |
| 6,206,957 B1 | 3/2001 | Driessens et al. |
| 6,281,195 B1 | 8/2001 | Rueger et al. |
| 6,281,257 B1 | 8/2001 | Ma et al. |
| 6,294,187 B1 | 9/2001 | Boyce et al. |
| 6,297,213 B1 | 10/2001 | Oppermann et al. |

(Continued)

FOREIGN PATENT DOCUMENTS

EP 0495284 7/1992

(Continued)

OTHER PUBLICATIONS

Lindholm et al., "Granular Hydroxyapatite and Allogeneic Demineralized Bone Matrix in Rabbit Skull Defect Augmentation" Annales Chirurglae et Gynacologiae, vol. 82, pp. 91-98, 1993.

(Continued)

*Primary Examiner*—Allison M Ford
(74) *Attorney, Agent, or Firm*—Harness, Dickey

(57) ABSTRACT

A bone graft material comprising about 50-90% quickly bioresorbable porogen particles and about 10-50% of a calcium matrix material. A bioactive substance can be included in the matrix material, the porogen particles, or both. Commercial packages containing the bone graft materials and methods for repairing bone therewith are also claimed.

43 Claims, No Drawings

U.S. PATENT DOCUMENTS

| | | |
|---|---|---|
| 6,309,659 B1 | 10/2001 | Clokie |
| 6,326,018 B1 | 12/2001 | Gertzman et al. |
| 6,334,891 B1 | 1/2002 | Constantz et al. |
| 6,340,477 B1 | 1/2002 | Anderson |
| 6,372,257 B1 | 4/2002 | Marchosky |
| 6,383,519 B1 | 5/2002 | Sapieszko et al. |
| 6,395,036 B1 | 5/2002 | Czernuszka et al. |
| 6,437,018 B1 | 8/2002 | Gertzman et al. |
| 6,440,444 B2 | 8/2002 | Boyce et al. |
| 6,458,375 B1 | 10/2002 | Gertzman et al. |
| 6,502,120 B2 | 12/2002 | Beiu |
| 6,630,155 B1 | 10/2003 | Chandrashekar et al. |
| 6,685,626 B2 | 2/2004 | Wironen |
| 6,777,002 B1 | 8/2004 | Vauridel et al. |
| 2001/0014662 A1 | 8/2001 | Rueger et al. |
| 2001/0014667 A1 | 8/2001 | Chen et al. |
| 2001/0014830 A1 | 8/2001 | Kwan et al. |
| 2001/0016646 A1 | 8/2001 | Rueger et al. |
| 2001/0018614 A1 | 8/2001 | Bianchi |
| 2002/0018796 A1 | 2/2002 | Wironen |
| 2002/0062154 A1 | 5/2002 | Ayers |
| 2002/0071827 A1 | 6/2002 | Petersen et al. |
| 2002/0098222 A1 | 7/2002 | Wironen et al. |
| 2002/0110541 A1 | 8/2002 | Petersen |
| 2003/0103960 A1* | 6/2003 | Philippart et al. ......... 424/94.64 |
| 2004/0137032 A1 | 7/2004 | Wang |
| 2004/0254639 A1 | 12/2004 | Li et al. |

FOREIGN PATENT DOCUMENTS

| | | |
|---|---|---|
| EP | 0522569 | 1/1993 |
| WO | WO 96/39203 | 12/1996 |
| WO | WO 98/40113 | 9/1998 |
| WO | WO 99/38543 | 8/1999 |
| WO | WO 00/45734 | 8/2000 |
| WO | WO 00/45870 | 8/2000 |
| WO | WO 00/54821 | 9/2000 |
| WO | WO 00/74690 | 12/2000 |
| WO | WO 03/011957 | 2/2003 |
| WO | WO 2004/091435 | 10/2004 |

OTHER PUBLICATIONS

Ambrosio et al., A Novel Amorphous Calcium Phosphate Polymer Ceramic for Bone Repair: I. Synthesis and Characterization, J Biomed Mater Res (Appl Biomater) 58: 295-301, 2001.

Burkus, Overview of Bone Grafting, Section 1 of 7 from Medscape Continuing Medical Education Course entitled: New Bone Graft Techniques and Applications in the Spine, www.medscape.com/viewarticle/443902, Nov. 7, 2002 (6 pages).

Gunatillake et al., Biodegradable Synthetic Polymers for Tissue Engineering, European Cells and Materials, vol. 5 (2003), pp. 1-16.

Iooss et al., A new injectable bone substitute combining poly(epsilon-caprolactone) microparticles with biphasic calcium phosphate granules, Biomaterials Oct. 2001; 22(20): 2785-94.

Laurencin et al., Bone Graft Substitute Materials, eMedicine, http://www.emedicine.com/orthoped/topic611.htm, pp. 1-10.

Leroux et al., Effects of various adjuvants (lactic acid, glycerol, and chitosan) on the injectability of a calcium phosphate cement, Bone Aug. 1999, 25 (2 Suppl): 31S-34S.

Linhart et al., Biologically and chemically optimized composites of carbonated apatite and polyglycolide as bone substitution materials, J Biomed Mater Res 54: 162-171, 2001.

Middleton et al., Synthetic Biodegradable Polymers as Medical Devices, Medical Devicelink, http://www.devicelink.com/grabber.php3?URL=http://www.devicelink.com/mpb/archive/98/03/002.html, (Mar. 1998), pp. 1-18.

Renner et al., Pedicle Screw Pull-Out Strength is Augmented by an Injectable Calcium Phosphate Cement and Varies by Injection Method, Society for Biomaterials 28th Annual Meeting Transactions, (2002), p. 81.

Simon et al., Preliminary report on the biocompatibility of a moldable, resorbable, composite bone graft consisting of calcium phosphate cement and poly(lactide-co-glycolide) microspheres, Journal of Orthopaedic Research 20 (2002) 473-482.

Togawa, Compressive Strength and Resorption Rates of Five Injectable Bone Cements Using a Rabbit Femoral Defect Model, Society for Biomaterials 28th Annual Meeting Transactions, (2002), p. 263.

Wu et al., In vitro degradation of three-dimensional porous poly(D,L-lactide-co-glycolide) scaffolds for tissue engineering, Biomaterials 25 (2004), pp. 5821-5830.

Beruto et al., Use of alpha-tricalcium phosphate (TCP) as powders and as an aqueous dispersion to modify processing, microstructure, and mechanical properties of polymethylmethacrylate (PMMA) bone cements and to produce bone-substitute compounds, J Biomed Mater Res, 49(4):498-505 (2000).

Damien et al., Effect of demineralized bone matrix on bone growth within a porous HA material: a histologic and histometric study, J Biomater Appl, 9(3):275-288 (1995).

Dunn et al., BMP gene delivery for alveolar bone engineering at dental implant defects, Molec Ther, 11(2):294-299 (2005).

Edwards et al., Sonic hedgehog gene-enhanced tissue engineering for bone regeneration, Gene Ther, 12:75-86 (2005).

Fujishiro et al., Preparation and compressive strength of alpha-tricalcium phosphate/gelatin gel composite cement, J Biomed Mater Res, 54(4):525-530 (2001).

Gerhart et al., In vitro characterization and biomechanical optimization of a biodegradable particulate composite bone cement, J Biomed Mater Res, 22(11):1071-1082 (1988).

Ignatius et al., Composites made of rapidly resorbable ceramics and poly(lactide) show adequate mechanical properties for use as bone substitute materials, J Biomed Mater Res, 57(1):126-131 (2001).

Kim et al., Effect of a calcium sulfate implant with calcium sulfate barrier on periodontal healing in 3-wall intrabony defects in dogs, J Periodontol, 69(9):982-988 (1998).

Li et al., The experimental study of repairing bone defects with allogeneic bone matrix gelatin and plaster, Chinese J Reparative and Reconstructive Surgery, 13(3):137-140 (1999).

Lindholm et al., Granular hydroxyapatite and allogeneic demineralized bone matrix in rabbit skull defect augmentation, Ann Chir Gynaecol, 82:91-98 (1993).

Lopez et al., Nacre, osteogenic and osteoinductive properties, Bull Inst Oceanogr (Monaco), 14(3):49-57 (1995).

Muggli et al., Reaction behavior of biodegradable, photo-cross-linkable polyanhydrides, Macromolecules, 31:4120-4125 (1998).

Nagaishi, The effect of various implant materials on cementogenesis, Nippon Shishubyo Gakkai Kaishi, 31(2):551-572 (1989).

Pereira-Mouries et al., Soluable silk-like organic matrix in the nacreous layer of the bivalve Pinctada maxima—a new insight in the biomineralization field, Eur J Biochem, 269:4994-5003 (2002).

Schmitz et al., A preliminary study of the osteogenic potential of a biodegradable alloplastic-osteoinductive alloimplant, Clin Orthop, 237:245-255 (1988).

Wilkins et al., Bioassayed demineralized bone matrix and calcium sulfate: use in bone-grafting procedures, Ann Chir Gynaecol, 88(3):180-185 (1999).

Driessens, F. et al. "Effective Formulations for the Preparation of Calcium Phosphate Bone Cements" Journal of Material Science: Materials in Medicine, 1994, vol. 5, pp. 164-170.

* cited by examiner

COMPOSITE BONE GRAFT MATERIAL

CROSS-REFERENCE TO RELATED APPLICATIONS

The present application is a continuation-in-part of copending U.S. patent application Ser. No. 11/105,334, filed Apr. 13, 2005.

BACKGROUND

The present invention involves the field of bone graft materials. A multiplicity of bone graft materials has been provided in the art for repairing defects in bone, including materials for adhering bone graft and implants to bone surfaces. These typically have taken the form of calcium phosphate-based or gel-based materials. In order to enhance the rate of resorption of such materials, porous forms of these materials have been created. In many cases, this involves administration of a bone graft material that contains a significant proportion of empty pores, with the concomitant risk of friability, the bone graft being brittle and subject to fragmentation. In some cases, biodegradable porogen particles have been used. However, the selection of materials and sizes for porogen particles often results in formation of pores too small for osteoblast colonization, or pores that take unduly long to form by in vivo biodegradation of the porogen, thus interfering with an efficient healing process. In some instances, porogens are used, but at such a low percentage (e.g., 20-50%) that efficient resorption of the, e.g., calcium phosphate or other matrix material is delayed. Thus, there is still a need for improved bone graft materials to speed the healing process, while providing for minimal load capability.

SUMMARY

The present teachings provide an improved bone graft material comprising a calcium matrix material and quickly resorbable porogen particles, the composition containing from about 50% to about 90% by volume porogen particles; and optionally containing bioactive substance(s).

The present teachings further provide:

Bone graft materials having a calcium matrix component, comprising calcium phosphate compounds(s) and salt(s), and having porogen particles, in a porogen particle-to-matrix material ratio of 1:1 to about 9:1;

Such bone graft materials in which the porogen particles comprise osteoinductive demineralized bone matrix; such materials in which the porogen particles comprise biocompatible, biodegradable polymer(s); such materials in which the porogen particles comprise biocompatible, biodegradable polymer(s) having a weight average molecular weight of about 2,000 to about 100,000;

Such bone graft materials in which the porogen particles comprise at least one bioactive agent; such materials in which the porogen particles include at least one morphology that is substantially regular polyhedral, lenticular, ovate, or spherical; such materials in which the porogen particles have one or more or all of their axial, transverse, or lateral dimensions in the range from about 100 to about 500 microns; such materials in which the porogen particles have a ratio of average width to average length that is from about 5:1 to about 1:5;

Such bone graft materials in which the porogen particles are solid, hollow, or laminate particles; such bone graft materials in which the porogen particles, or at least one wall or layer thereof, are capable of biodegradation in vivo in about 10 minutes to about 8 weeks.

Such bone graft materials that are in the form of a paste, injectible solution or slurry, dry powder, or dry solid; such bone graft materials that are in the form of a paste, injectible solution or slurry that has been hydrated by application of a biological fluid to a dry powder or dry solid bone graft material;

Commercial packages containing such a bone graft material and instructions for use thereof in repairing bone; and Methods for repairing bone by providing such a bone graft material and administering it to a living bone tissue surface in need thereof; such methods further comprising permitting the material to remain at an in vivo site in which it is placed, for a sufficient time to permit porogen particles thereof to be biodegraded in vivo.

It has been discovered that the present compositions and methods afford advantages over bone graft materials known in the art, including one or more of enhanced rates of integration, calcium matrix resorption, and osteoblast colonization. Further uses, benefits and embodiments of the present teachings are apparent from the description set forth herein.

DETAILED DESCRIPTION

Glossary

The following definitions and non-limiting guidelines must be considered in reviewing the description set forth herein. The headings (such as "Introduction" and "Summary,") and sub-headings (such as "Compositions" and "Methods") used herein are intended only for general organization of topics within the description, and are not intended to limit the disclosure of the teachings or any aspect thereof. In particular, subject matter disclosed in the "Introduction" can include aspects of technology within the scope of the teachings, and may not constitute a recitation of prior art. Subject matter disclosed in the "Summary" is not an exhaustive or complete disclosure of the entire scope of the invention or any embodiments thereof. Classification or discussion of a material within a section of this specification as having a particular utility (e.g., as being a "system") is made for convenience, and no inference should be drawn that the material must necessarily or solely function in accordance with its classification herein when it is used in any given composition.

The citation of references herein does not constitute an admission that those references are prior art or have any relevance to the patentability of the invention disclosed herein. Any discussion of the content of references cited in the Introduction is intended merely to provide a general summary of assertions made by the authors of the references, and does not constitute an admission as to the accuracy of the content of such references. All references cited in the Description section of this specification are hereby incorporated by reference in their entirety.

The description and specific examples, while indicating embodiments of the invention, are intended for purposes of illustration only and are not intended to limit the scope of the invention. Moreover, recitation of multiple embodiments having stated features is not intended to exclude other embodiments having additional features, or other embodiments incorporating different combinations the stated of features. Specific Examples are provided for illustrative purposes of how to make and use the compositions and methods disclosed and, unless explicitly stated otherwise, are not intended to be a representation that given embodiments of this invention have, or have not, been made or tested.

As used herein, the words "preferred" and "preferably" refer to embodiments of the teachings that afford certain benefits, under certain circumstances. However, other embodiments can also be preferred, under the same or other circumstances. Furthermore, the recitation of one or more preferred embodiments does not imply that other embodiments are not useful, and is not intended to exclude other embodiments from the scope of the teachings.

As used herein, the term "about," when applied to the value for a parameter of a composition or method hereof, indicates that the calculation or the measurement of the value allows some slight imprecision without having a substantial effect on the chemical or physical attributes of the composition or method.

The term "a" as used herein means at least one.

As used herein, the word "include," and its variants, is intended to be non-limiting, such that recitation of items in a list is not to the exclusion of other like items that can also be useful in the present materials, compositions, devices, and methods.

Although the open-ended term "comprising," as a synonym of terms such as including, containing, or having, is used herein to describe and claim the present subject matter, this can alternatively be described using more limiting terms such as "consisting of" or "consisting essentially of" the recited ingredients. Thus, for example, in some embodiments, a bone graft material hereof comprises a combination of about 10-25% of a calcium-based matrix material and about 75-90% by volume biodegradable porogen particles, but the composition can contain almost solely those two components, or can consist or consist essentially of those components.

Bone Graft Materials

A bone graft material according to the present teachings can comprise a calcium-based matrix material and porogen particles, as further defined below, the ratio of porogen particles to matrix material being from about 1:1 to about 9:1. The matrix can, in addition, contain other substances that collectively comprise about 10% by volume or less of the matrix, in some embodiments, about 5% or less, about 3%, about 2% or about 1% or less of the matrix. The porogen particles can make up about 50% to about 90% by volume of the bone graft material; or about 75% to about 90%. The matrix material component makes up the remainder. In some embodiments, the porogen particles can be susceptible to biodegradation within about 10 minutes to about 8 weeks; within 10 minutes to about 6 weeks, about 10 minutes to about 4 weeks, about 10 minutes to about 2 weeks, or about 10 minutes to about 1 week.

A bone graft material according to the present teachings provides an osteoinductive scaffold for promoting bone healing, as well as for enhanced colonization by osteoblasts, even without use of expensive osteoinductive factors in the porogen particles, which factors are thus optional therein. The material can support a minimal load. Further advantages of the composition can include: ease and economy of manufacturing, increased proportion of porogen particles and enhanced biodegradation rate of the selected porogen material enhances development of in vivo porosity to expedite bone cell colonization, increase the rate of calcium phosphate matrix resorption, and decrease the time needed for healing; the ability to wet or suffuse the composition with autologous biological fluids to thereby further enhance the healing properties of the material; the lack or reduced frequency of empty pores in the material as administered can reduce the immediate potential for the material to be friable as a result of different resorption rates of component materials.

A bone graft material according to the present teachings can be provided in the form of a bone paste, a shaped solid, or a dry pre-mix useful for forming such a paste or solid. The phrase "bone paste" refers to a slurry or semi-solid composition of any consistency that hardens to form a solid structure, and thus includes, e.g., bone plasters, putties, adhesives, cements, bone void fillers, and bone substitutes. As a result, the bone paste can be any composition capable of being injected, molded, painted, suffused, or placed into contact with a bone surface in vivo. The "shaped solid" can take any form, including a pellet that can be placed into a bone void or into contact with a bone surface in vivo. The dry pre-mix can be provided in the form of a powdered and/or granular material.

Calcium Matrix Component

A calcium matrix component (CMxC) for use herein can comprise, or can be formed from a composition comprising, at least one of: 1) a combination of a calcium sulfate material and a calcium carbonate material, 2) a calcium carbonate sulfate material, 3) a combination of a calcium sulfate material and a calcium carbonate sulfate material, or 4) a combination of a calcium carbonate material and a calcium carbonate sulfate material, said CMxC being pharmaceutically acceptable. As used herein, a CMxC is one in which the sum of the calcium and sulfate and carbonate present therein is at least 50% by dry weight (i.e. anhydrous weight, which excludes water of crystallization, adsorbed water, and so forth, as well as liquids provided by wetting solutions and the like) of the CMxC. In some embodiments, the sum of these three can be about 60% or more, about 70% or more, about 75% or more, about 80% or more, about 85% or more, about 90% or more, about 95% or more, or about 100% by dry weight of the CMxC; in some embodiments, the sum of these three can be up to an approximate value of 70%, 75%, 80%, 85%, 90%, 95%, or 100% by dry weight of the CMxC. In various embodiments, the molar ratio of carbonate to phosphate can be within a range from about 1:10 to about 10:1 or from about 1:5 to about 5:1; the molar ratio can be about 1:3 or more, about 3:1 or less, about 1:2 or more, about 2:1 or less, or about 1:1. In some embodiments, the sum of the sulfate and carbonate present in a CMxC can be 30% or more by dry weight of the CMxC, or at least or about: 35%, 40%, 45%, 50%, 55%, or 60% by dry weight of the CMxC; in various such embodiments, the sum of these two can be up to or about: 70%, 65%, 60%, 55%, 50%, 45%, 40%, or 35% by dry weight of the CMxC.

A CMxC for use herein can, in some embodiments, further comprise, or be formed from a composition comprising, a calcium phosphate material. In various embodiments, in which a calcium phosphate material is used, the amount of phosphate present in the CMxC can be less than 50% by dry weight of the CMxC; in some embodiments, the amount of phosphate present in the CMxC can be about or less than: 40%, 35%, 30%, 25%, 20%, 15%, 10%, or 5% by dry weight of the CMxC; in some such embodiments, the amount of phosphate present in the CMxC can be about 1% or more, about 5% or more, about 10% or more, about 15% or more, about 20% or more, or about 25% or more by dry weight of the CMxC.

As used herein, a calcium sulfate material can be or can comprise any one or more of the following in anhydrous or hydrated, amorphous or crystalline form(s): calcium sulfate ($CaSO_4$), calcium sulfate hemihydrate ($CaSO_4.H_2O$), calcium sulfate dihydrate ($CaSO_4.2H_2O$); calcium-replaced calcium sulfates; sulfate-replaced calcium sulfates; and calcium- and sulfate-replaced calcium sulfates.

Calcium-replaced calcium sulfates as used herein, are homologs of calcium sulfate, $Ca_x(SO_4)_x$, in which some of, e.g., a minority of (such as about or less than: 40%, 35%, 33.3%, 30%, 25%, 20%, 15%, or 10% of) the calcium are substituted with monovalent and/or divalent metal cation(s), e.g., sodium or potassium homologs thereof, such as $Na_2Ca(SO_4)_2$ and $K_2Ca_2Mg(SO_4)_4$.

Sulfate-replaced calcium sulfates, as used herein, are homologs of calcium sulfate, $Ca_x(SO_4)_x$ in which some of, e.g., a minority of (such as about or less than: 40%, 35%, 33.3%, 30%, 25%, 20%, 15%, or 10% of) the sulfate groups are substituted with phosphate, hydrogen phosphate, hydroxide, halide (e.g., F, Cl, and/or I), and/or silicate groups, e.g., calcium phosphate sulfates, such as $Ca_2HPO_4SO_4$.

Calcium- and sulfate-replaced calcium sulfates, as used herein, are homologs of calcium sulfate, $Ca_x(SO_4)_x$, in which both some of, e.g., a minority of, the calcium groups and some of, e.g., a minority of, the sulfate groups are substituted as described above, e.g., $Ca_3Mn(SO_4)_2(OH)_6$.

As used herein, a calcium carbonate material can be or can comprise any one or more of the following in anhydrous or hydrated, amorphous or crystalline form(s): calcium carbonate ($CaCO_3$), calcium carbonate hydrate $CaCO_3.H_2O$, calcium carbonate dihydrate $CaCO_3.2H_2O$; calcium-replaced calcium carbonates; carbonate-replaced calcium carbonates; and calcium- and carbonate-replaced calcium carbonates.

Calcium-replaced calcium carbonates as used herein, are homologs of calcium carbonate, $Ca_x(CO_3)_x$, in which some of, e.g., a minority of (such as about or less than: 40%, 35%, 33.3%, 30%, 25%, 20%, 15%, or 10% of), the calcium are substituted with monovalent and/or divalent metal cation(s), e.g., sodium, magnesium, or potassium homologs thereof, such as sodium, magnesium, or potassium calcium carbonates, e.g., $Na_2Ca(CO_3)_2$, $MgCa(CO_3)_2$, or $K_2Ca(CO_3)_2$.

Carbonate-replaced calcium carbonates as used herein are homologs of calcium carbonate, $Ca_x(CO_3)_x$, in which some of, e.g., a minority of (such as about or less than: 40%, 35%, 33.3%, 30%, 25%, 20%, 15%, or 10% of), the carbonates are substituted with phosphate, hydrogen phosphate, hydroxide, halide (e.g., F, Cl, and/or I), and/or silicate groups e.g., $Ca(CO_3)_2HPO_4$, $Ca_2CO_3(OH)_2$.

Calcium- and carbonate-replaced calcium carbonates are homologs of calcium carbonate, $Ca_x(CO_3)_x$, in which both some of, e.g., a minority of, the calcium groups and some of, e.g., a minority of, the carbonate groups are substituted as described above As used herein, a calcium carbonate sulfate material can be or can comprise any one or more of the following in anhydrous or hydrated, amorphous or crystalline form(s): calcium carbonate sulfate, $Ca_2(CO_3)SO_4$; calcium-replaced calcium carbonate sulfates; carbonate/sulfate-replaced calcium carbonate sulfates; and calcium- and carbonate/sulfate-replaced calcium carbonate sulfates.

Calcium-replaced calcium carbonate sulfates, as used herein, are homologs of calcium carbonate sulfate, $Ca_x(CO_3)_{x-n}(SO_4)_n$ (0<n<x), in which some, e.g., a minority of (such as about or less than: 40%, 35%, 33.3%, 30%, 25%, 20%, 15%, or 10% of), the calcium groups are substituted with monovalent and/or divalent metal cation(s).

Carbonate/sulfate-replaced calcium carbonate sulfates, as used herein, are homologs of calcium carbonate sulfate, $Ca_x(CO_3)_{x-n}(SO_4)_n$ (0<n<x), in which some of, e.g., a minority of (such as about or less than: 40%, 35%, 33.3%, 30%, 25%, 20%, 15%, or 10% of) the sulfate and/or carbonate groups are substituted with phosphate, hydrogen phosphate, hydroxide, halide (e.g., F, Cl, and/or I), and/or silicate groups.

Calcium- and carbonate/sulfate-replaced calcium sulfates, as used herein, are homologs of calcium carbonate sulfate, $Ca_x(CO_3)_{x-n}(SO_4)_n$ (0<n<x), in which both some of, e.g., a minority of, the calcium groups and some of, e.g., a minority of, the sulfate and/or carbonate groups are substituted as described above, e.g., $Ca_3Mn(SO_4)(CO_3)(OH)_6$ and $Ca_6Mg_2(SO_4)_2(CO_3)_2Cl_4(OH)_4$.

As used herein, a calcium phosphate material can be or can comprise any one or more of the following in anhydrous or hydrated, amorphous or crystalline form(s):

a) calcium phosphate salts or compounds, such as: tricalcium phosphate $Ca_3(PO_4)_2$ (TCP), including alpha-TCP, beta-TCP, and biphasic calcium phosphate containing alpha- and beta-TCP; amorphous calcium phosphate (ACP); monocalcium phosphate $Ca(H_2PO_4)_2$ (MCP) and monocalcium phosphate monohydrate $Ca(H_2PO_4)_2.H_2O$ (MCPM); dicalcium phosphate $CaHPO_4$ (DCP) and dicalcium phosphate dihydrate $CaHPO_4.2H_2O$ (DCPD); tetracalcium phosphate $Ca_4(PO_4)_2O$ (TTCP); octacalcium phosphate $Ca_8(PO_4)_4(HPO_4)_2.5H_2O$ (OCP);

b) calcium apatite salts or compounds, such as: calcium hydroxyapatite $Ca_{10}(PO_4)_6(OH)_2$ (CHA); calcium oxyapatite $Ca_{10}(PO_4)_6O$ (COXA); calcium carbonate apatite $Ca_{10}(PO_4)_6CO_3$ (CCA); calcium carbonate hydroxyapatites, e.g., $Ca_{10}(PO_4)_5(OH)(CO_3)_2$ and $Ca_{10}(PO_4)_4(OH)_2(CO_3)_3$ (CCHA);

c) calcium-deficient calcium phosphate or apatite salts or compounds in which the molar or mass ratio of Ca:P is reduced by about 20% or less, or about 15% or less, or about 10% or less, relative to the corresponding calcium-non-deficient species, examples of which include: calcium-deficient hydroxyapatites, e.g., $Ca_{10-x}(HPO_4)_x(PO_4)_{6-x}(OH)_{2-x}$ ($0 \leq X \leq 1$) (CDHA); calcium-deficient carbonate hydroxyapatites (CDCHA), and calcium-deficient carbonate apatites (CDCA).

d) other calcium phosphate or apatite salts or compounds known as useful in the bone graft material field, e.g.: calcium polyphosphates; further calcium apatites having a general formula of $Ca_{10}T_6D$ or $Ca_{10}T_6M_2$ or $Ca_{15}T_9[iii]$, wherein T is a trivalent tetrahedral compound anion, such as an $XO_4^{3-}$ (X=metal or phosphorus) anion, D is a divalent anion, M is a monovalent anion, and [iii] is an anion or combination of anions that is trivalent, such further calcium apatites being pharmaceutically acceptable; and calcium-, phosphate-, and/or hydroxyl-"replaced" calcium phosphates, further described below.

Calcium-replaced calcium phosphates or apatites, as used herein, are homologs of any of the above calcium phosphates or apatites (a-d) in which some of, e.g., a minority of (such as about or less than: 40%, 35%, 33.3%, 30%, 25%, 20%, 15%, or 10% of) the calciums are substituted with monovalent and/or divalent metal cation(s), e.g., sodium calcium homologs thereof, such as $CaNa(PO_4)$.

Phosphate-replaced calcium phosphates or apatites, as used herein, are homologs of any of the above calcium phosphates or apatites (a-d) in which some of, e.g., a minority of (such as about or less than: 40%, 35%, 33.3%, 30%, 25%, 20%, 15%, or 10% of) the phosphate groups are substituted with carbonate, sulfate, hydrogen phosphate, and/or silicate groups, e.g., calcium phosphate-sulfate $Ca_2HPO_4SO_4$.

Hydroxyl-replaced calcium phosphates or apatites, as used herein, are homologs of any of the above calcium phosphates or apatites (a-d) in which some of the hydroxyl-containing materials, e.g., a minority of (such as about or less than: 40%, 35%, 33.3%, 30%, 25%, 20%, 15%, or 10% of) the hydroxyl groups are substituted with F, Cl, and/or I, and/or $CO_3$.

In some embodiments of a calcium-replaced homolog of any of the above materials, the monovalent metal cation can be an alkali metal cation, such as sodium; or it can be Cu(I); or a combination thereof. In some embodiments of a calcium-replaced homolog, the divalent metal cation can be an alkaline earth metal, such as beryllium, magnesium, strontium, and/or barium, or magnesium, strontium, and/or barium, or magnesium; in some embodiments of a calcium-replaced homolog, the divalent metal cation can be a divalent transition metal, such as chromium, cobalt, copper, manganese, and/or zinc; or a combination thereof.

In some embodiments of a hydroxyl-replaced homolog, the halide can be fluoride, chloride, and/or iodide; or the halide can be fluoride and/or chloride. Examples of such hydroxyl-replaced homologs can include, e.g., calcium haloapatites, calcium haloahydroxypatites, and calcium halooxyapatites, the latter having a formula of, e.g., $Ca_{15}(PO_4)_9(X)O$ wherein X is F, Cl, or I.

In some embodiments a composition according to the present teachings is prepared from a composition comprising at least one calcium sulfate material and at least one calcium carbonate material or comprising at least one calcium carbonate sulfate material; in some embodiments, the composition will be prepared from the former materials.

In some embodiments, the calcium sulfate material can be calcium sulfate ($CaSO_4$). In some embodiments, the calcium carbonate material can be calcium carbonate ($CaCO_3$).

Other Matrix Components

The matrix material for a bone graft material according to the present teachings can optionally contain other additives, for example: inorganic additives, including e.g., silicates, iron oxides, and the like; plasticizing agents, including lubricants and the like; binding agents, including thickeners and the like; and/or bioactive agents, including osteoinductive factors, non-osteo-specific growth factors, medicaments, osteoclast inhibitors (e.g., bisphosphonate analogs of pyrophosphate [i.e. $(H_2PO_3)$—CH(R)—$(H_2PO_3)$, $(H_2PO_3)$—C(=R)—$(H_2PO_3)$, or $(H_2PO_3)$—C(R)(R')—$(H_2PO_3)$]), and the like. In some embodiments, the additives can collectively comprise about 10% by volume or less of the matrix, or about 5% or less, or about 3%, about 2%, or about 1% or less of the matrix.

In some embodiments, a bone graft material according to the present teachings can include a plasticizing agent. In some embodiments, plasticizing agents can include: powdered demineralized bone matrix, such as powdered human or bovine DBM; one or more polyether, such as a cellulose derivative, e.g., methylcellulose, carboxymethylcellulose, ethylcellulose, hydroxyethylcellulose, hydroxypropyl methylcellulose, cellulose acetate butyrate, salts thereof, and combinations thereof; and alcohols and polyols of at least three carbon atoms in length, e.g., oleyl alcohol, glycerol, sorbitol, xylitol, propylene glycol, butylene glycol, polyethylene glycol, and vinyl alcohols (polyvinylalcohols). In various embodiments, a cellulose derivative can be used as the plasticizer in plasticizing-agent-containing embodiments of the present teachings.

In some embodiments, bioactive agents for use in the present teachings can include: bone morphogenic proteins (BMPs), bone-derived growth factors (e.g., BDGF-2), transforming growth factors (e.g., TGF-beta), somatomedins (e.g., IGF-1), platelet-derived growth factors (PDGF), and fibroblast growth factors (FGF); general growth hormones (e.g., somatotropin) and other hormones; pharmaceuticals, e.g., anti-microbial agents, antibiotics, antiviral agents, microbistatic or virustatic agents, anti-tumor agents, and immunomodulators; and metabolism-enhancing factors, e.g., amino acids, non-hormone peptides, vitamins, and minerals; and natural extracts.

In some embodiments, the matrix material can be at least substantially free of one or more of: gelatin; calcium sulfate; low molecular weight (e.g., C2-C6) esters, diols, and triols; pentaerythritol and sorbitol; synthetic biodegradable polymers, such as polyhydroxyalkanoates, e.g., PGA, PLA, and PHB polymers and copolymers; and polypeptides. In some embodiments, the matrix material can be at least substantially free all of the above components, or about free, or free thereof.

Porogen Particles

In some embodiments according to the present teachings, the bone graft material can comprise porogen particles in combination with the matrix material. In some embodiments of a porogen particle-containing bone graft material, the composition can contain about 50% to about 90% by volume porogen particles. In some embodiments, the bone graft material can comprise about 55% or more by volume porogen particles, or about 60% or more, about 65% or more, about 70% or more, about 75% or more, about 80% or more, or about 85% or more by volume porogen particles. In some embodiments, the composition can contain about 90% or less by volume porogen particles. In some embodiments, the composition can contain about 75% to about 90% porogen particles.

In some embodiments, the composition can contain 80% or more by volume porogen particles, or more than 80%, or about 81% or more, or 81% or more, or more than 81%, or about 82% or more, or 82% or more, or more than 82%, or about 83% or more, or 83% or more, or more than 83%, or about 84% or more, or 84% or more, or more than 84%, or 85% or more or more than 85%. In some embodiments, the composition can contain from 80% to about 90% by volume porogen particles, or from more than 80% to about 90% porogen particles. In some embodiments, the composition can contain from about 85% to about 90% porogen particles.

Porogen particles useful herein can be made of any biocompatible, biodegradable substance that can be formed into a particle capable of at least substantially retaining its shape during processing of the bone graft material and until subjected to biodegradation-type conditions, e.g., in vivo conditions. Such substances can also be referred to herein as porogen particle materials or porogen particle "wall" materials.

The biocompatible, biodegradable substance(s) for the porogen particles can be inorganic or organic. In some embodiments, the biocompatible, biodegradable substance selected can be an organic polymer, such as a synthetic organic polymer, e.g., poly(vinyl alcohol), or a combination thereof with another polymer or a bioactive substance. Alternatively, or in addition, the organic, biocompatible, biodegradable substance can comprise demineralized bone matrix, and/or a mono-, di-, or poly-saccharide. In some embodiments, the biocompatible, biodegradable substance selected can be: a calcium salt or compound; sodium chloride; or a mixture thereof; or a calcium phosphate or mixture thereof; or a combination of any of the foregoing comprising a bioactive substance.

In some embodiments, the porogen particles can have a morphology that is any one or more of at least substantially cylindrical, at least substantially prismatic, at least substantially pyramidal, at least substantially regular polyhedral, at least substantially paraboloidal, at least substantially lenticular, at least substantially ovate, or at least substantially spherical. In some embodiments, the porogen particles can include those that are at least substantially regular polyhedral, at least substantially lenticular, at least substantially ovate, or at least substantially spherical. The porogen particles can be "solid" particles, i.e. non-hollow, non-laminar particles containing the biocompatible, biodegradable substance(s); they can be hollow particles having at least one wall defining an internal "empty" space, i.e. one that is devoid of a wall material, but that can be filled with a different solid or fluid material, e.g., a bioactive substance; or they can be laminar particles having a core and at least one distinct layer, the core and layer(s) thereof being independently any wall material, the layers of the particle not defining an "empty" space, but being positioned adjacent one to the next. Hollow particles include those particles that have both laminar features and hollow space(s).

Porogen particles for use in an embodiment of the present teachings can have at least one dimension (i.e. axial, transverse, or lateral dimension) that is about 100 to about 500 microns. In one embodiment, all porogen particles of a given morphology can have at least one average axial, transverse, or lateral dimension that is about 100 to about 500 microns. In some embodiments, all porogen particles used can independently have at least one axial, transverse, or lateral dimension that is about 100 to about 500 microns. In some embodiments, all porogen particles used can collectively have at least one average axial, transverse, or lateral dimension that is about 100 to about 500 microns.

In some embodiments, at least one dimension of the porogen particles can be about 100 microns or more, or about 120 microns or more, or about 140 microns or more. In some embodiments, at least one dimension of the porogen particles can be about 500 microns or less, about 425 microns or less, about 350 microns or less, about 300 microns or less, or about 250 microns or less. In some embodiments, the porogen particles can have at least one dimension that is about 120 to about 350 microns. In some embodiments, these gradations also apply to independent, average, and/or collective dimensions as described above. In some embodiments, at least two of the axial, transverse, and lateral dimensions of the particle can independently be about 100 to about 500 microns; in some embodiments, the axial, transverse, and lateral dimensions of the particle can independently be about 100 to about 500 microns.

In some embodiments, the porogen particles can have a ratio of average width (lateral and transverse dimensions) to average length (main axial dimension) that is about 5:1 to about 1:5, or about 4:1 to about 1:4, about 3:1 to about 1:3, about 2:1 to about 1:2; in some embodiments, the porogen particles can have a ratio of average width to average length that is about 1:1.

In some embodiments, the porogen particles used in the bone graft material can have at least about the same morphology. In some embodiments, the porogen particles used in the bone graft material can have at least about the same morphology and at least about the same size.

Polymers for Porogen Particles

In some embodiments of a porogen particle-containing bone graft material, the particles can comprise a biodegradable, biocompatible polymer. For purposes of the present teachings, a biodegradable polymer is considered a biocompatible polymer if it is not unduly immunogenic (according to a reasonable risk-benefit analysis in sound medical judgment), and does not biodegrade to form undesirable insoluble deposits or toxic byproducts that cannot be further catabolized in vivo to form non-toxic products. Similar definitions apply for other biodegradable, biocompatible substances useful herein.

Common classes of biodegradable, biocompatible polymers useful herein include: polyesters, including polyhydroxyalkanoates, polylactones (e.g., polycaprolactones), and poly(propylene fumarates); polyanhydrides, e.g., poly(sebacic anhydride); tyrosine-derived polycarbonates (see, e.g., Muggli et al., *Macromolecules* 31:4120-25 (1998)); polyorthoesters; copolymers of any one or more of these with one another and/or with other biocompatible polymerizable units; and the biodegradable, biocompatible polymers described in U.S. Pat. No. 6,630,155 to Chandrashekar et al. and U.S. Pat. No. 6,777,002 to Vuaridel et al.; and US Patent Publication No. 2004/0254639 to Li et al.

The monomers from which the biocompatible, biodegradable polymers useful herein are made can be C1-C18 monomers, such as: C2-C12, C2-C10, C2-C8, C2-C6, or C2-C4 monomers. The polymers hereof can be homopolymers or heteropolymers of any conformation, e.g., linear, branched (including hyperbranched), cross-linked, or cyclic, etc. Useful copolymers can be statistical, random, alternating, periodic, block, or graft copolymers. By way of example, biodegradable polyhydroxyalkanoate copolymers useful herein can be, e.g., lactide, glycolide, or hydroxybutyrate copolymers synthesized with: other hydroxyacyl monomers, segments, or branches; polyalkylene oxide monomers, segments, or branches; diol or polyol monomers, segments, or branches, such as polyalkylene glycol (e.g., polyethylene or polypropylene glycol) monomers, segments, or branches; carbohydrate (including sugar alcohol, sugar acid, and other sugar derivative) monomers, segments, or branches; amino acyl monomers, segments, or branches; and/or other biocompatible polymerizable units.

Examples of polyhydroxyalkanoate polymers include: poly(lactide) polymers, poly(glycolide) polymers, and poly(hydroxybutyrate) polymers, wherein the monomer units from which these are formed can have any chirality or combination of chiralities; copolymers that represent combinations of these; and copolymers that represent a combination of any of the foregoing with another hydroxyacid monomer or polymerizable monomer of another type. Examples of polyhydroxyalkanoate polyester polymers include poly(glycolide), poly(L-lactide), poly(D,L-lactide), poly(L-lactide-co-glycolide), poly(L-lactide-co-D,L-lactide), poly(D,L-lactide-co-glycolide), poly(3-hydroxybutyrate), poly(3-hydroxybutyrate-co-3-hydroxyvalerate), and poly(glycolide-co-trimethylene carbonate).

The (weight average) molecular weight of biodegradable polymers typically used in bone tissue substitute materials, and which can be used in some embodiments hereof, are, e.g.: about 2,000 or more, about 5,000 or more, about 10,000 or more, about 20,000 or more, about 30,000 or more, about 40,000 or more, or about 50,000 or more MW; about 100,000 or less, about 90,000 or less, about 80,000 or less, about 70,000 or less, about 60,000 or less, or about 55,000 or less MW; and about 2,000 to about 100,000 MW, more typically about 5,000 to about 100,000 MW, about 10,000 to about 90,000 MW, about 20,000 to about 80,000, about 30,000 to about 70,000, or about 40,000 to about 60,000 MW, with about 50,000 to about 55,000 MW being common. Any such molecular weight biocompatible, biodegradable polymer can be used in an embodiment of the present teachings, and can be selected in conjunction with other factors that influence porogen particle in vivo degradation rates.

In vivo degradation rates for biocompatible, biodegradable polymers are discussed, e.g., in P A Gunatillake & R. Adhikari, Biodegradable synthetic polymers for tissue engineering, *Eur. Cells & Mater.* 5:1-16 (2003); and J C Middleton & A J Tipton, Synthetic biodegradable polymers as medical devices, *Med. Plastics & Biomater.* March/April 1998:30-39 (March 1998). In vitro degradation rates for 10 mm diameter cylindrical samples of polyhydroxyalkanoates are described in L Wu & J Ding, In vitro degradation of three-dimensional porous poly(D,L-lactide-co-glycolide) scaffolds for tissue engineering, *Biomaterials* 25:5821-30 (2004). Based on these data, the following estimated approximate rates of degradation can be typically expected for biodegradable polymers commonly used in bone graft materials.

TABLE 1

Typical Degradation Rates for Selected Biocompatible, Biodegradable Polymers

| Polymer | Rate |
|---|---|
| Poly(L)LA | 45 μm/wk |
| Poly(e-caprolactone) | 45 |
| Poly(D,L)LA | 90 |
| PGA | 140 |
| PGA-co-Me$_3$-carbonate | 140 |
| Copoly(D,L)L/GA 85:15 | 260 |
| Poly(propylene-fumarate) | 330 |
| Copoly(D,L)L/GA 75:25 | 520 |
| Copoly(D,L)L/GA 50:50 | 770 |

In Table 1: Poly(L)LA is poly(L-lactic acid); poly(e-caprolactone) is poly(epsilon-caprolactone); poly(D,L)LA is poly(D-,L-lactic acid); PGA is poly(glycolic acid); PGA-co-Me3-carbonate is poly(glycolic acid-co-trimethylene carbonate); copoly(D,L)UGA 85:15, 75:25, and 50:50 are poly(D-,L-lactic acid-co-glycolic acid) polymers respectively having approximate molar proportions of 85:15, 75:25, and 50:50 lactic acid:glycolic acid monomers; and poly(propylene-fumarate) is poly(propylene glycol-co-fumaric acid).

Resorption rates, as used herein, refer to rates of resorption for individual particles that are directly in contact with biological fluid at least in part, e.g., along at least one surface zone thereof. It can be understood that many uses of a bone graft material can produce an in vivo mass of bone graft material in contact with bone tissue, the mass of bone graft material containing both porogen particles partly embedded along a surface of the mass, and thus directly exposed to biological fluid, and porogen particles buried within the mass. Those porogen particles that are buried most distally from biological fluid sources may not be resorbed until a point in time later than that at which the original surface-exposed particles will have become resorbed, particularly in the case where the porogen particle material is or includes substance(s), such as demineralized bone matrix or other biomineralizing organic matrix materials, that are mainly resorbed by action of cells, rather than by contact with fluid alone. However, use of quickly resorbing porogen particles in the bone graft material, as taught herein, reduces the overall time until resorption of the mass' entire population of particles of a given type is complete.

Although the microns-per-week resorption rates recited in Table 1 can be typical for in vitro degradation of commonly used versions of these polymers (e.g., typically having a 50,000-55,000 MW), a variety of factors can result in different degradation rates. For example, use of a relatively lower molecular weight version of a particular polymer would be expected to increase the overall rate of degradation and dissolution of the polymer in vivo. Alternatively, use of a copolymer formed from that polymer's units with another, more hydrolysable species, e.g., a hydroxyacid and a biologically hydrolyzable carbohydrate(s) or peptide(s), would be expected to increase the rate of bulk degradation, since hydrolysis of the, e.g., carbohydrate or peptide units enhances fragmentation, resulting in lower molecular weight polymer substrates as an intermediate for degradative dissolution. Other factors and their relative effects on degradation rates for a given polymer are likewise known to one of ordinary skill in the art, e.g., polymer architecture, particle shape (geometry), particle morphology (internal structure, e.g., solid, hollow, laminar, etc.), surface area-to-volume ratio, degree of encapsulation in matrix, pH of the local in vivo environment, and accessibility of in vivo fluids and/or cells to the polymer.

Demineralized Bone Matrix

In some embodiments, a porogen particle-containing bone graft material, the particles can comprise osteoinductive demineralized bone matrix (DBM) or an osteoinductive substitute therefor; or a mixture of DBM or DBM substitute with a biodegradable polymer as described above. In some embodiments, the osteoinductive demineralized bone matrix (DBM), can be at least substantially demineralized (about 90% or more), about fully demineralized (about 95% or more, about 97%, 98%, or 99% or more), or fully demineralized. The bone provided for demineralization can be cancellous and/or cortical bone, or other bony tissue, e.g., tooth tissue (e.g., dentine) or antler tissue; in some embodiments, it can be cancellous and/or cortical bone. The DBM can be prepared from bone of the species for which the bone graft material is to be used. In the case of humans, the DBM can be prepared from, e.g., human, bovine, porcine, ovine, caprine, equine, cervine, piscine, or avian bone; or human, bovine, porcine, or ovine bone; or human, bovine, or porcine bone; or human or bovine bone; or human bone. In some embodiments, a DBM-containing porogen particle can contain solely DBM; in some embodiments, the DBM can be combined with at least one further substance, e.g., a biodegradable polymer or a bioactive agent or both.

Alternatively to DBM, a DBM substitute can be prepared from demineralized proteinaceous matrix obtained from another biomineralized material, such as from another biomaterial in which the biomineralization comprises calcium compounds or salts. Examples of demineralized non-bone matrix materials include demineralized non-bony tissues, such as mollusk shells, brachiopod shells; avian shells; otoliths, otoconia; and invertebrate exoskeletons, tests, and related structures, e.g., of bryozoans, cnidarians, and echinoderms. In some embodiments, a DBM substitute can be or comprise demineralized mollusk or brachiopod shell such as demineralized mollusk nacre or brachiopod semi-nacre, which comprise the inner, non-prismatic shell layer(s), whether composed of, e.g., a nacreous, crossed-lamellar, or other microstructure(s); in some embodiments, demineralized mollusk shell can be used, or demineralized mollusk nacre.

Demineralized bone and substitute matrix materials can be prepared by any of the methods known in the art, examples of which include treatment of the mineralized tissue, or fragments or particles thereof, with inorganic (e.g., HCl) or organic acid solutions and/or chelator(s) such as EDTA or EGTA, and other procedures, as described, e.g., in U.S. Pat. No. 6,189,537 to Wolfinbarger. The demineralized bone matrix or substitute, or the mineralized tissue from which it is prepared, can be further processed, e.g., by irradiation, sterilization, lyophilization, or any other desired useful technique known in the art.

The demineralized bone matrix so prepared can be obtained directly from the demineralization process as an osteoinductive material, i.e. retaining its native bone-growth-promoting factors. Osteoinductive factors native to such materials include, e.g.: bone morphogenetic proteins (BMPs), such as osteocalcin, osteogenin, and osteonectin. Demineralized non-bony tissue matrix materials can also provide some degree of osteoinductivity through the presence of other bioactive factors native thereto. See, e.g.: E. Lopez et al., Nacre, osteogenic and osteoinductive properties, *Bull. Inst. Oceanogr.* (Monaco) 14:49-58 (1993); and L. Pereira-Mouriès et al., *Eur. J. Biochem.* 269:4994-5003 (2002). However, a demineralized non-bony tissue matrix, where used, can be supplemented with osteoinductive factor(s). Where osteoinductive factors are added to a demineralized bone matrix or substitute, they can be factors that the subject to receive the bone graft material can use to foster osteogenesis; they can be from the same species as that of the subject; or from the same individual. In the case of peptide-type factors, the term "same" includes, e.g., identity of amino acid sequence, regardless of the organism synthesizing the peptide.

An osteoinductive demineralized bone matrix (DBM) or osteoinductive substitute can be provided by supplementing a non-osteoinductive demineralized bone, or a non-osteoinductive substitute demineralized non-bony tissue matrix, with osteoinductive factors. Non-osteoinductive demineralized bone matrix is described, e.g., in U.S. Pat. No. 6,685,626 to Wironen. In some embodiments, DBM or a DBM substitute retaining its native osteoinductive factors can be used. In some embodiments, DBM or a DBM substitute can be used that has been prepared by supplementing a non-osteoinductive demineralized tissue matrix with osteoinductive factors, such as BMPs, e.g., by mixing it or infusing it with, or bonding to it, such factors. Any DBM (i.e. osteoinductive DBM) or any osteoinductive DBM substitute can be further supplemented with, e.g., additional osteoinductive factors or other bioactive agents.

The osteoinductive DBM or substitute can be provided in the form of any micro- or macro-particles of any morphology, including, e.g.: powders, granulates, chips, and flakes; gel formats (e.g., hydrogels, hydrogels in a carrier, such as a glycerol carrier) are also useful. Where the DBM or substitute is to be used as the porogen, it can be provided in the form of particles having the porogen particle size, geometry, and morphology parameters described herein; such particles can comprise either single fragments or aggregates of the DBM and/or DBM substitute.

Compared to the preferred synthetic polymers described for porogen particles, DBM and its substitutes typically resorb at a somewhat slower rate, e.g., in some cases about 10-20 microns per week. DBM, which is typically derived from cortical bone, possesses an inherent porosity since cortical bone contains a network of approximately 20-50 micron channels (Haversian canals). Therefore, it is not necessary for DBM and DBM substitutes to resorb at the same rate as a porogen material lacking such small-diameter porosity, in order to obtain cellular penetration and calcium matrix resorption rates provided by the present teachings. In some embodiments in which porogen particles are DBM or a DBM substitute, these particles can have a diameter(s) in the range of 100 to about 750 microns. In some embodiments of this type, the presence of such small-diameter channels allows cellular penetration in the porogen particles while providing osteoinductive factors for cell conversion and proliferation. In some embodiments for obtaining particle DBM or DBM substitutes having particle dissolution times of about a week or less, the particles thereof can have at least one, or two, or all three of the axial, lateral, and transverse dimensions in the range of about 10 to about 100 microns, or about 10 to about 50, about 10 to about 40, about 10 to about 30, about 10 to about 25, or about 10 to about 20 microns. In some embodiments, clusters of DBM particles in which the particles have such dimensions, such as in the range of about 10 to about 50 microns, can be used, wherein the clusters have one, two, or three average dimensions that are from about 100 to about 500 microns. Such clusters of smaller particles can also be employed for non-DBM or non-DBM substitute materials, such as synthetic polymers as described above, and can be included for those that resorb at rate less than 100 microns per week.

In some embodiments of DBM-containing or DBM substitute-containing clusters, the smaller particles making up the cluster can be a combination of DBM or DBM substitute small particles and synthetic polymer small particles. In some embodiments, porogen particles of about 100 to about 500 micron dimensions can be used that contain an admixture of a DBM or DBM substitute with one or more biocompatible, biodegradable polymer, selected from those having a resorption rate of about 100 microns per week or more. In some embodiments, a bone graft material comprising 100 to 500 micron DBM or DBM substitute porogen particles, both such porogen particles, and more quickly resorbing polymer porogen particles can be present within the matrix. In such an embodiment, the DBM or DBM substitute porogen particles can resorb over a period of about 6 to about 8 weeks, while the polymeric porogen particles can resorb at a rate of about 1 week or less.

Porogen Particle Additives

The material chosen for the substance of the porogen particle bulk, wall(s)/layer(s), and/or core structures can be a pure substance, as any of the polymers and copolymers, compounds, and whole (processed) tissues and tissue fragments described above, or it can be a mixture of such substances. Where a mixture is used, it can comprise any combination of the above-described porogen particle materials in any proportions. The mixture can further comprise a minority of any one or more agents that are: processing aids, such as binders (e.g., cellulose ethers) and lubricants (e.g., fatty acids); storage aids, such as preservatives and dryness-promoting agents; rehydration aids, such as wetting-facilitation agents; alginate; and the like. In some embodiments, such agents can constitute less than 20%, or about 15% or less, or about 10% or less, or about 5% or less, or about 4% or less, or about 3% or less, or about 2% or less, or about 1% or less of the mixture. Thus, the material provided for the substance of the porogen particle can be any such compound or mixture.

The porogen particles can further contain one or more added bioactive agent, either: (1) encapsulated in one or more hollow space(s) within a "hollow" particle; or (2) located within or throughout the bulk of a "solid" particle, or of a core, wall, or layer of a hollow or laminar particle. Examples of bioactive agents for use in an embodiment of the present teachings are: bone morphogenic proteins (e.g., BMP1-BMP15), bone-derived growth factors (e.g., BDGF-1, BDGF-2), transforming growth factors (e.g., TGF-alpha, TGF-beta), somatomedins (e.g., IGF-1, IGF-2), platelet-derived growth factors (e.g., PDGF-A, PDGF-B), fibroblast growth factors (e.g., αFGF, βFGF), osteoblast stimulating factors (e.g., OSF-1, OSF-2), and sonic hedgehog protein (SHH); other hormones, growth factors, and differentiation factors (e.g., somatotropin, epidermal growth factor, vascular-endothelial growth factor; osteopontin, bone sialoprotein, α2HS-glycoprotein; parathyroidhormone-related protein, cementum-derived growth factor); biogenic proteins and tissue preparations (e.g., collagen, carbohydrates, cartilage); gene therapy agents, including naked or carrier-associated nucleic acids (e.g., single- or multi-gene constructs either alone or attached to further moieties, such as constructs contained within a plasmid, viral, or other vector), examples of which include nucleic acids encoding bone-growth-promoting polypeptides or their precursors, e.g., sonic hedgehog protein (see, e.g., P C Edwards et al., *Gene Ther.* 12:75-86 (2005)), BMPs (see, e.g., C A Dunn et al., *Molec. Ther.* 11(2):294-99 (2005)), Runx2, or peptide hormones, or antisense nucleic acids and nucleic acid analogs, e.g., for inhibiting expression of bone-degradation-promoting factors; pharmaceuticals, e.g., anti-microbial agents, antibiotics, antiviral agents, microbistatic or virustatic agents, anti-tumor agents, and immunomodulators; and metabolism-enhancing factors, e.g., amino acids, non-hormone peptides, vitamins, minerals, and natural extracts (e.g., botanical extracts). The bioactive agent preparation can itself contain a minority of, e.g., processing, preserving, or hydration enhancing agents. Such bioactive agents or bioactive agent preparations can be used in either the porogen particle(s) or the calcium matrix material, or both. Where both contain bioactive agent(s), the agent(s) can be the same or different.

In some embodiments, a plurality of different porogen particles can be used, which can differ in any desired ways, e.g., in size, morphology, bulk material, bioactive agent(s), and/or other additives. Porogen particles having the dimensions and characteristics described herein can also be used in combination with "other porogens" that can resorb at a different rate or rates, or that can be of a different size (e.g., nanoparticles) or morphology (e.g., fibrous or filamentous) than the "porogen particles" described herein. Examples of such uses include the use of polymer "porogen particles" along with slower-resorbing DBM particles or with DBM small-particle clusters. Thus, a bone graft material according to the present teachings can comprise a combination of "porogen particles" as defined herein, with "other porogens" known in the art. In some embodiments, at least half of, or at least a majority of, the porogens in a bone graft material according to the present teachings can be "porogen particles" having the characteristics as defined herein. In a preferred embodiment, about 60% or more, about 70% or more, about 75% or more, about 80% or more, about 85% or more, about 90% or more, about 95% or more, or about 98% or more of the total volume of porogens in the composition can be comprised of "porogen particles" as defined herein. In some embodiments, at least substantially about all, or about all, or all of the porogens in a composition according to the present teachings can be "porogen particles" as defined herein.

In some embodiments in which one or more bioactive agent preparation is included in the bulk of a solid particle or core, wall, or layer of a hollow or laminar particle, the additive (s) can make up about 10% or less by volume of the material, about 5% or less, about 4% or less, about 3% or less, about 2% or less, or about 1% or less. The maximal amount of bioactive agent preparation included in a space in a hollow particle can be determined by the volume of the space. The format for additives to be included in porogen particles according to the present teachings can be powders, particles, or solutions of any morphology or consistency (e.g., dry, paste, or slurry), provided that the additives can be effectively incorporated into either the bulk substance of the porogen particle or into a void within.

Porogen Particle Parameter Selection

Regardless of the formulation of the biocompatible material selected for a porogen particle, e.g., whatever the identity of a biocompatible biodegradable polymer selected, for use in a given embodiment of the present teachings, any of the techniques described in the above-cited references, in the articles cited therein, and in other references known in the art, can be used to obtain approximate biodegradation rates therefor, whether relative or absolute. These rates can then be used to select a dimension for a particular geometry or morphology desired for in vivo biodegradation over a selected time period. For example, where degradation is desired over a period of 3 days, and the desired geometry-plus-morphology is a substantially spherical "solid" microparticle partly embedded in a ceramic- or glass-type matrix and having at least one exposed surface, the particle diameter could be about 220 microns for a polymer that degrades at a rate of about 520 microns per week. Likewise, where a 3-day degradation period is desired for a similarly situated, single-walled hollow microparticle, the wall thickness could be about 20 microns for a polymer that degrades at a rate of about 45 microns per week.

In some embodiments according to the present teachings, the biocompatible, biodegradable polymer or DBM or DBM substitute to be used, can be selected in light of other biodegradation-rate influencing factors, to obtain either: porogen particles that contain the polymer, DBM or substitute, or of a polymer-, DBM-, or DBM substitute-bioactive ingredient combination throughout the bulk of the particle (i.e. are neither hollow nor laminar), and which can be biodegraded in vivo within about 10 minutes to about 7 days; or porogen particles that are hollow or laminar particles having at least one wall or layer that is made of the polymer or solid polymer-bioactive ingredient combination, at least one wall of which can be biodegraded in vivo within about 10 minutes to about 7 days, i.e. that average time to dissolution in vivo for the particle or wall is a value within that range. In some embodiments, the polymer or polymeric combination can be selected in conjunction with other particle parameters to obtain porogens in which average time to dissolution in vivo for the particle or wall is within about 10 minutes to about 5 days, or about 10 minutes to about 3 days.

Preparation of the Bone Graft Material

The matrix material and porogen particle components, and other optional components, selected for a bone graft material according to the present teachings can be combined in any order. In some embodiments, the matrix material and porogen particle components can be pre-mixed, with optional inclusion of other matrix additives; and then a bioactive substance (s) can be combined therewith. Alternatively, a bioactive substance(s) can be optionally included in the matrix material(s) and/or in the porogen particles before they are combined.

The bone graft material, where provided in a hydratable form, e.g., a dry powdered or granulated form or a dry solid block or plug form or any semi-solid form, can be wetted or further wetted with a wetting agent to produce a wetted format, such as a paste, putty, or pre-wetted solid for administration to a subject. In some embodiments of a wetted composition, the liquid used for wetting can be a neat solution or a biological fluid. Where a neat solution is used, it can be an aqueous saline or a buffered aqueous solution, such as phosphate-buffered saline or a cell growth medium, having a biocompatible pH (e.g., about pH6 to about pH8, or about pH 6.5 to about pH 7.5); the biocompatible pH can be inherent to the wetting liquid before use, or can be a result of applying the liquid to the composition. Where a biological fluid is used, it can be biocompatible with the subject to be treated with the bone graft material, e.g., not unduly immunogenic or toxic to the individual to receive it, in accordance with a reasonable risk-benefit ratio assessed in sound medical judgment. In some embodiments, the biological fluid can be autologous to the patient to be treated.

Useful biological fluids from complex animals and humans can be vascular or extra-vascular. Examples of such biological fluid wetting agents include, but are not limited to: blood, serum, platelet concentrate, bone marrow aspirate, and synovial fluid. A biological fluid can be used in the form obtained from the biological source, or it can be processed by application of one ore more desired useful techniques, examples of which include, separation techniques, such as filtration (macro-, micro-, or ultra-filtration); purification techniques, such as dialysis; concentration techniques; and sterilization techniques.

The neat solution or biological fluid can further be supplemented with one or more additives. Examples of additives include, but are not limited to: medicaments; polypeptides, including enzymes, proteins, and proteinaceous tissue preparations; peptide hormones and growth factors; non-peptide hormones and growth factors; vitamins; minerals; and the like.

The bone graft material, or components thereof, can be treated to contain or harbor, internally or externally, living cells. The cells can be subject-autologous cells, subject-matched donor cells, or subject-compatible cultured cells. Example of such cells include, e.g.: osteoblasts; pluripotent stem cells, such as osteoblast precursors (e.g., adipose tissue-derived and bone-marrow derived stem cells); and totipotent stem cells. In some cell-containing embodiments these can be applied to the bone graft material by suffusing it with a neat solution or biological fluid containing such cells.

Commercial Packages

A commercial package can provide a bone graft material according to the present teachings as a pre-moistened paste or other semi-solid or liquid formulation; or it can provide the bone graft material as a dry powder or solid. Where the bone graft material is supplied in a dry form, an aqueous solution can be provided in the commercial package for use in wetting the dry material. For example, an ionic solution, such as saline, or a buffered solution, such as phosphate-buffered saline, can be provided. A commercial package can contain instructions for use, and optionally for further preparation of the bone graft material prior to use. The commercial package can optionally contain a device or devices for use in mixing, shaping, and/or administering (e.g., inserting, injecting, or applying) the bone graft material.

The description of the teachings is merely exemplary in nature and, thus, variations that do not depart from the gist of the teachings are intended to be within the scope of the teachings. Such variations are not to be regarded as a departure from the spirit and scope of the teachings.

What is claimed is:

1. A bone graft material having a calcium matrix component and porogen particles;
   wherein said calcium matrix component comprises calcium carbonate sulfate; and
   wherein the porogen particles make up between 65% and 90% by volume of the bone graft material.

2. The bone graft material according to claim 1, wherein said calcium matrix component further comprises a calcium phosphate material.

3. The bone graft material according to claim 1, wherein said calcium matrix component further comprises at least one plasticizing agent, at least one bioactive agent, or a combination thereof.

4. The bone graft material according to claim 1, wherein said porogen particles comprise at least one biocompatible, biodegradable substance.

5. The bone graft material according to claim 4, wherein said biocompatible, biodegradable substance is osteoinductive demineralized bone matrix (DBM) or an osteoinductive DBM substitute.

6. The bone graft material according to claim 5, wherein said DBM is human or bovine DBM and said DBM substitute is osteoinductive-factor-supplemented demineralized mollusk nacre.

7. The bone graft material according to claim 4, wherein said biocompatible, biodegradable substance is a biocompatible, biodegradable polymer.

8. The bone graft material according to claim 7, wherein said biocompatible, biodegradable polymer is a biocompatible, biodegradable polyester, polyanhydride, tyrosine-derived polycarbonate, polyorthoester, or polymer blend containing at least one such polymer.

9. The bone graft material according to claim 7, wherein said biocompatible, biodegradable polymer is a biocompatible, biodegradable polyester.

10. The bone graft material according to claim 9, wherein said biocompatible, biodegradable polyester is a biocompatible, biodegradable polyhydroxyalkanoate.

11. The bone graft material according to claim 10, wherein said biocompatible, biodegradable polyhydroxyalkanoate is formed from hydroxyl-carboxylic acid monomers independently containing about 2 to about 6 carbon atoms, from lactone forms thereof, or from a combination thereof.

12. The bone graft material according to claim 11, wherein the average size of said carboxylic acid monomers is about 2 to about 4 carbon atoms.

13. The bone graft material according to claim 7, wherein the biocompatible, biodegradable polymer has an average molecular weight of about 2,000 to about 100,000.

14. The bone graft material according to claim 7, wherein the biocompatible, biodegradable polymer has an average molecular weight of about 20,000 to about 80,000.

15. The bone graft material according to claim 7, wherein the biocompatible, biodegradable polymer has an average molecular weight of about 50,000 to about 55,000.

16. The bone graft material according to claim 1, wherein said porogen particles comprise at least one bioactive agent.

17. The bone graft material according to claim 1, wherein said porogen particles comprise at least substantially regular polyhedral, lenticular, ovate, or spherical particles, or a combination thereof.

18. The bone graft material according to claim 1, wherein said porogen particles collectively have at least one average axial, transverse, or lateral dimension that is about 100 to about 500 microns.

19. The bone graft material according to claim 1, wherein said porogen particles collectively have at least one average axial, transverse, or lateral dimension that is about 120 to about 425 microns.

20. The bone graft material according to claim 1, wherein said porogen particles collectively have at least one average axial, transverse, or lateral dimension that is about 120 to about 350 microns.

21. The bone graft material according to claim 1, wherein each of the average axial, transverse, and lateral dimensions of the porogen particles is independently about 100 to about 500 microns.

22. The bone graft material according to claim 1, wherein each of the average axial, transverse, and lateral dimensions of the porogen particles is independently about 120 to about 425 microns.

23. The bone graft material according to claim 1, wherein each of the average axial, transverse, and lateral dimensions of the porogen particles is independently about 120 to about 350 microns.

24. The bone graft material according to claim 1, wherein said porogen particles have a ratio of average width to average length that is from about 5:1 to about 1:5.

25. he bone graft material according to claim 1, wherein said porogen particles have a ratio of average width to average length that is from about 2:1 to about 1:2.

26. The bone graft material according to claim 1, wherein said porogen particles have a ratio of average width to average length that is about 1:1.

27. The bone graft material according to claim 1, wherein said porogen particles make up about 70% to about 90% by volume of the bone graft material.

28. The bone graft material according to claim 1, wherein said porogen particles make up about 75% to about 90% by volume of the bone graft material.

29. The bone graft material according to claim 1, wherein said porogen particles make up about 80% to about 90% by volume of the bone graft material.

30. The bone graft material according to claim 1, wherein said porogen particles are solid particles.

31. The bone graft material according to claim 1, wherein said porogen particles are capable of being biodegraded in vivo in about 10 minutes to about 7 days, or wherein said porogen particles are DBM or DBM substitute porogen particles that are capable of being biodegraded in vivo in about 10 minutes to about 8 weeks, or said porogen particles comprise a combination of these porogen particles.

32. The bone graft material according to claim 1, wherein said porogen particles are hollow or laminar particles.

33. The bone graft material according to claim 32, wherein at least one wall or layer of said porogen particles is capable of being biodegraded in about 10 minutes to about 7 days, or wherein at least one wall or layer of said porogen particles is DBM or a DBM substitute wall or layer that is capable of being biodegraded in vivo in about 10 minutes to about 8 weeks, or said porogen particles comprise a combination of these hollow or laminar particles.

34. The bone graft material according to claim 1, wherein said material is provided in the form of a paste, injectable solution or slurry, dry powder, or dry solid.

35. The bone graft material according to claim 1, wherein said material is provided in the form of a paste, injectable solution or injectable slurry.

36. The bone graft material according to claim 1, wherein said porogen particles include a plurality of first porogen particles comprising osteoinductive DBM or osteoinductive DBM substitute, and a plurality of second porogen particles comprising a biocompatible, biodegradable polymer or polymers.

37. The bone graft material according to claim 29, wherein said material is provided in the form of a paste, injectable solution or slurry, dry powder, or dry solid.

38. The bone graft material according to claim 29, wherein said material is provided in the form of a paste, injectable solution, or injectable slurry, and said porogen particles independent have an average axial, transverse, and lateral dimensions of about 120 to about 350 microns.

39. A commercial package containing a bone graft material according to claim 1 and instructions for use thereof in repairing bone.

40. A method for repairing bone comprising:
providing a bone graft material according to claim 1; and
administering said bone graft material to a living bone tissue surface in need thereof.

41. The method according to claim 40, said method further comprising permitting said material to remain at an in vivo she in which it is placed, for a sufficient time to permit the porogen particles thereof to be biodegraded in vivo.

42. A commercial package containing a bone graft material according to claim 29 and instructions for use thereof in repairing bone.

43. A method for repairing bone comprising:
providing a bone graft material according to claim 29; and
administering said bone graft material to a living bone tissue surface in need thereof.

* * * * *

UNITED STATES PATENT AND TRADEMARK OFFICE
CERTIFICATE OF CORRECTION

PATENT NO. : 7,621,963 B2 Page 1 of 1
APPLICATION NO. : 11/402312
DATED : November 24, 2009
INVENTOR(S) : Bruce J. Simon et al.

It is certified that error appears in the above-identified patent and that said Letters Patent is hereby corrected as shown below:

Col. 1, line 44: "compounds(s)" should be -- compound(s) --

Col. 2, line 60: "the stated of" should be -- of the stated --

Col. 5, line 46: a -- . -- should be inserted after "above"

Col. 7, line 16: "haloahydroxypatites" should be -- haloahydroxyapatites --

Col. 11, line 29: "UGA" should be -- L/GA --

Col. 14, line 40: "wefting-facilitation" should be -- wetting-facilitation --

Col. 17, line 7: "ore" should be -- or --

Col. 19, line 8 (claim 25): "he bone" should be -- The bone --

Col. 20, line 30 (claim 41): "she" should be -- site --

Signed and Sealed this

Eighteenth Day of May, 2010

David J. Kappos
*Director of the United States Patent and Trademark Office*